(12) United States Patent
Lindberg

(10) Patent No.: US 7,963,908 B2
(45) Date of Patent: Jun. 21, 2011

(54) DEVICE TO LUBRICATE A PENIS OR MEDICAL APPARATUS

(76) Inventor: Kevin Lindberg, Grand Rapids, MI (US)

(*) Notice: Subject to any disclaimer, the term of this patent is extended or adjusted under 35 U.S.C. 154(b) by 489 days.

(21) Appl. No.: 11/978,393

(22) Filed: Oct. 29, 2007

(65) Prior Publication Data

US 2009/0112054 A1 Apr. 30, 2009

(51) Int. Cl.
*A61F 5/00* (2006.01)
(52) U.S. Cl. .......................................... 600/38
(58) Field of Classification Search ................ 604/172; 600/38–41; 184/18, 88.1, 88.2, 96, 102, 184/109; 401/265
See application file for complete search history.

(56) References Cited

U.S. PATENT DOCUMENTS

| | | | |
|---|---|---|---|
| 2,441,642 A | 5/1948 | McDaniel | |
| 2,847,880 A | 8/1958 | Neidig | |
| 3,805,770 A * | 4/1974 | Okada | 600/114 |
| 4,063,617 A | 12/1977 | Shenk | |
| 5,192,271 A * | 3/1993 | Kalb et al. | 604/116 |
| 5,242,428 A * | 9/1993 | Palestrant | 604/265 |
| 5,293,960 A * | 3/1994 | Majerowicz et al. | 184/13.1 |
| 5,445,243 A * | 8/1995 | Coffey et al. | 184/102 |
| 5,743,359 A * | 4/1998 | Parnell | 184/102 |
| 5,885,233 A | 3/1999 | Adachi | |
| 6,306,080 B1 | 10/2001 | Mitchell et al. | |
| 6,749,557 B2 | 6/2004 | Garland | |
| 2002/0055702 A1 | 5/2002 | Atala et al. | |
| 2004/0152948 A1 | 8/2004 | Kim | |

FOREIGN PATENT DOCUMENTS

WO WO 02/051493 * 7/2002

* cited by examiner

*Primary Examiner* — Samuel G Gilbert
(74) *Attorney, Agent, or Firm* — Price Heneveld Cooper DeWitt & Litton LLP

(57) ABSTRACT

A device to lubricate a penis or medical instrument before insertion into the human body or orifice is disclosed. The device can be made from a ring that is covered with one or more membranes and contains lubricating material within the interior volume defined by the ring and the membrane(s). Alternatively, the device can be made from a ring that surrounds foam that is saturated with lubricant. In either embodiment, the membrane(s) or foam contain a penetration zone defined by any number of intersecting slits. A method of using the same to lubricate a penis or a medical instrument, such as an endoscope.

10 Claims, 3 Drawing Sheets

DEVICE TO LUBRICATE A PENIS OR MEDICAL APPARATUS

BACKGROUND OF THE INVENTION

The present invention relates to devices that are used to lubricate a penis or medical apparatus, such as laparoscopy instruments, which include cameras and lights, and endoscopy instruments, which include endoscopes, before insertion into a human body.

BRIEF SUMMARY OF THE INVENTION

The device of the present invention includes a device that a user can use to lubricate a penis or medical apparatus. In one embodiment, the structural support of the device is a cylindrical ring or a relatively short tube. A thin and flexible material covers the top and bottom of the ring or relatively short tube. This material on the top and bottom of the structural support of the device creates a volume within the device. That volume contains a lubricating gel or other lubrication material. The material covering the top and bottom of the structural support of the device has a penetration zone defined by slits, such as a cruciform (two intersecting slits), three intersecting slits, four intersecting slits, and so on, within the material. The slits permit entry of the object to be lubricated but prevent leakage of the lubrication material contained within the device. The device can be constructed of inexpensive materials so as to permit the user to economically dispose of the device after using the device only once.

In another embodiment disclosed herein, the structural support of the device is again a cylindrical ring or a relatively short tube. A thin and flexible material covers only the bottom of the ring or relatively short tube. The inside of the structural support of the device and the bottom cover material creates a volume within the device (without a top cover). That volume contains a lubricating gel or other lubrication material. The material covering the bottom of the structural support of the device has a penetration zone defined by slits, such as a cruciform (two intersecting slits), three intersecting slits, four intersecting slits, and so on, within the material. The slits permit entry of the object to be lubricated but prevent leakage of the lubrication material contained within the device. The device can be constructed of inexpensive materials so as to permit the user to economically dispose of the device after using the device only once.

In yet another embodiment disclosed herein, the structural support of the device is again a cylindrical ring or a relatively short tube. The structural support surrounds a foam or sponge material that is saturated with lubricant. The sponge or foam material contains a penetration zone defined by slits, such as a cruciform slit, three intersecting slits, four intersecting slits, and so on, to permit access of the object to be lubricated. Again, the device can be constructed of inexpensive materials so as to permit the user to economically dispose of the device after using the device only once.

As the reader can appreciate from the above summary of the several embodiments disclosed herein are easy to use, easy to manufacture, not prone to breaking because of the non-incorporation of moveable parts, prevent leakage of the lubrication material yet permit lubrication of the object intended to be lubricated, and is economically disposable after a single use.

BRIEF DESCRIPTION OF THE SEVERAL VIEWS OF THE DRAWINGS

The accompanying drawings illustrate several embodiments in accordance with the present invention.

DETAILED DESCRIPTION OF THE INVENTION

Figure 1:
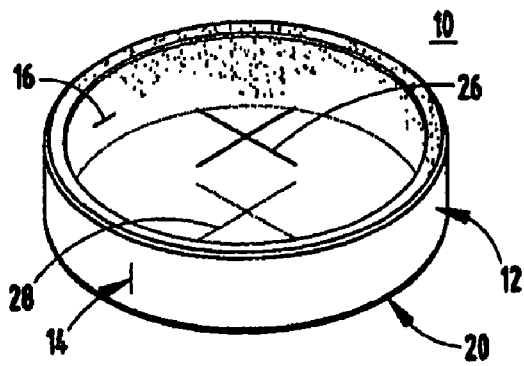
FIG. 1 is a top perspective view of a first embodiment of the lubrication device.
Figure 2:
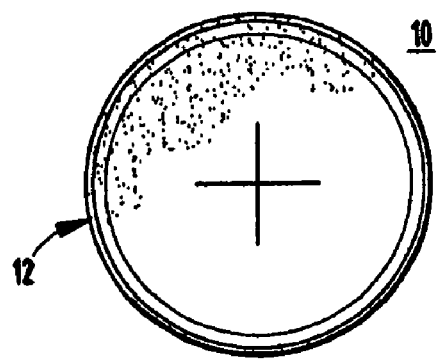
FIG. 2 is a top elevational view of the first embodiment of the lubrication device.
Figure 3:
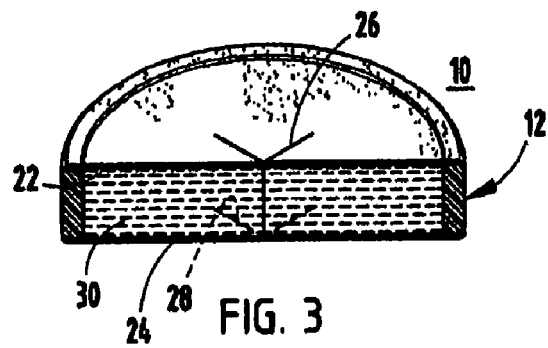
FIG. 3 is a cross-sectional perspective view of the first embodiment of the lubrication device.
Figure 4:
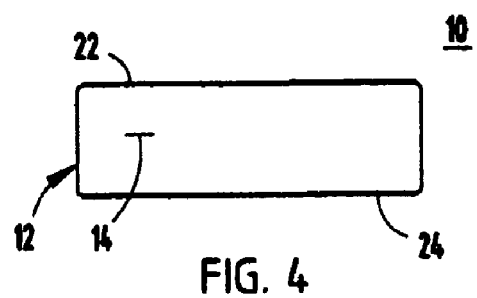
FIG. 4 is a side elevational view of the first embodiment of the lubrication device.
Figure 6:
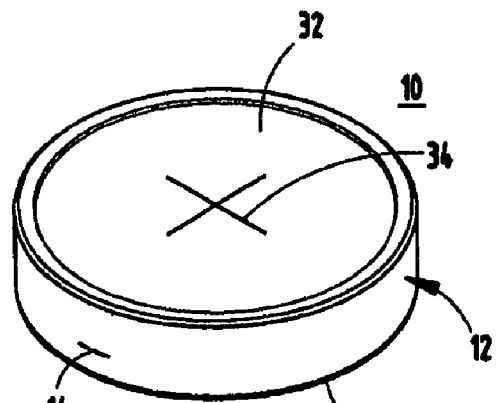
FIG. 6 is a top perspective view of a second embodiment of the lubrication device.
Figure 7:
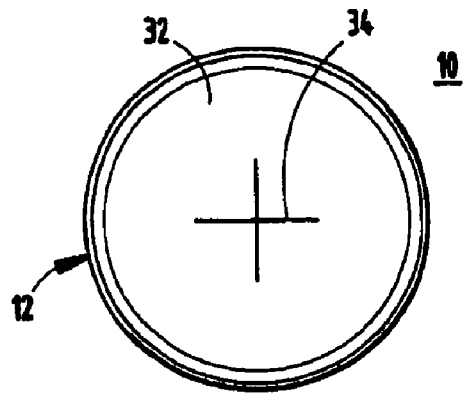
FIG. 7 is a top elevational view of the second embodiment of the lubrication device.
Figure 8:
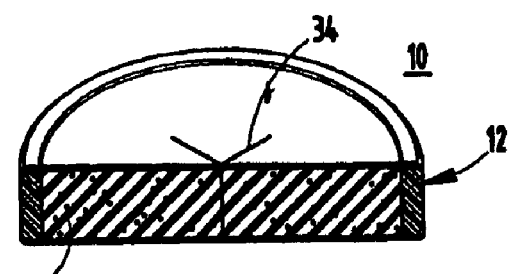
FIG. 8 is a cross-sectional perspective view of the second embodiment of the lubrication device.
Figure 9:
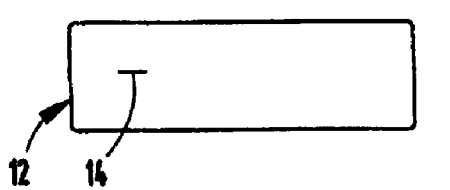
FIG. 9 is a side elevational view of the second embodiment of the lubrication device.
Figure 5:
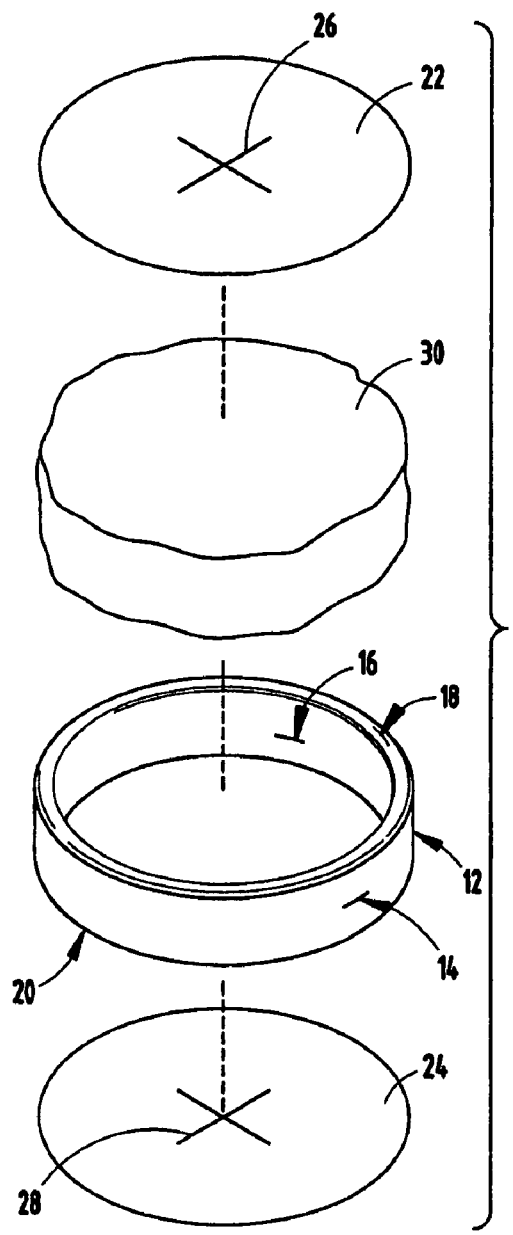
FIG. 5 is an exploded view of the first embodiment of the lubrication device.
Figure 10:
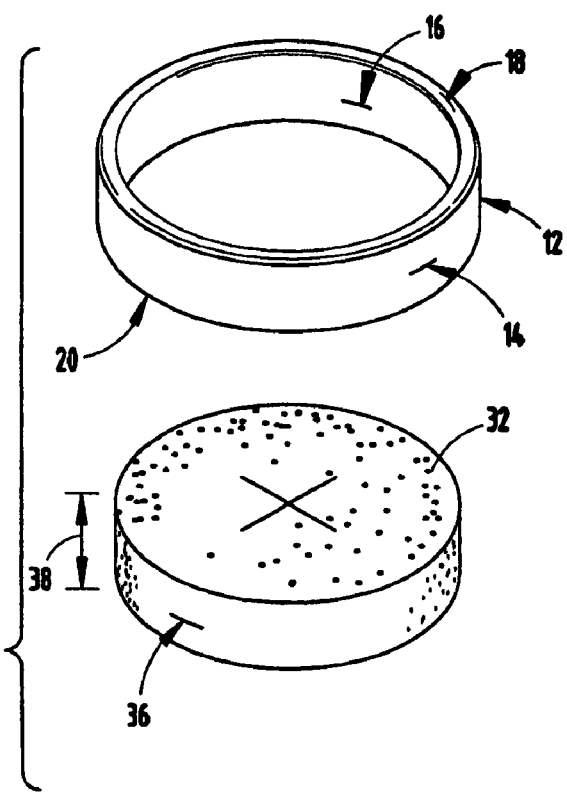
FIG. 10 is an exploded view of the second embodiment of the lubrication device.

Referring now to FIGS. 1 through 5, the structural support for the lubrication device 10 is provided in part by a ring 12. The ring 12 can be formed from any polymer material, such as PVC (polyvinyl chloride) or PE (polyethylene). The ring 12 could be made to whatever size that would suit the application, such as a ring 12 that has an inside diameter of 2 to 2.5 inches. The ring 12 has an outside perimeter surface 14, an inside perimeter surface 16, a top surface 18, and a bottom surface 20. The thickness of the ring 12, as defined as the distance from the top surface 18 to the bottom surface 20, is between approximately 0.25 and 0.38 inches. The inside diameter range and thickness range for the ring 12 must be suitable to lubricate a penis (the average penis has a diameter of 1.6 inches) and be suitable to evenly lubricate a laparoscopy tube.

Figure 12:
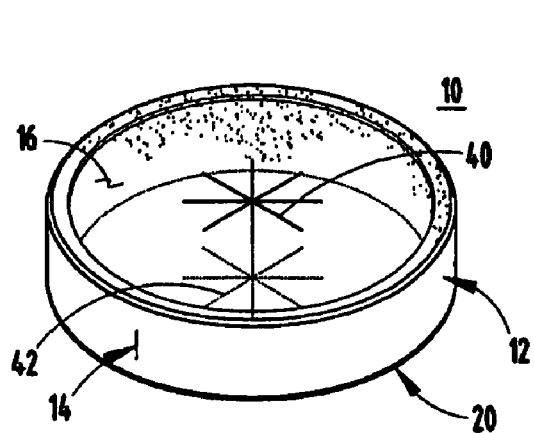
FIG. 12 is a top perspective view of the first embodiment of the lubrication device, where the penetration zone is defined by four intersecting slits rather than a cruciform slit.

A top membrane 22 is fixably attached to the top surface 18 of the ring 12. A bottom membrane 24 is fixably attached to the bottom surface 20 of the ring 12. The top membrane 22 has a top penetration zone defined by a top cruciform slit 26. The bottom membrane 24 contains a bottom penetration zone defined by a bottom cruciform slit 28. The top penetration zone and bottom penetration zone are not limited to cruciform slits; any number of slits in the top membrane 22 or bottom membrane 24, such as the top four intersecting slits 40 and bottom four intersecting slits 42 (as shown in FIG. 12). The reader should understand that any number of intersecting slits can make a penetration zone in the top membrane 22 or bottom membrane 24.

The top membrane 22 and the bottom membrane 24 can be made from polymer materials, such as polyethylene, or from plastic wraps, such as polyvinylidene chloride (PVdC) and low density polyethylene (LDPE). In that regard, Saran wrap is an acceptable membrane material. The top membrane 22 and the bottom membrane 24 can be attached to the ring 12 by the use of an adhesive, by ultrasonic welding, or by thermal bonding. The inventor has placed the cruciform slits into the membranes by perforating the membranes with a razor blade. Alternatively, a steel rule die could be used as well to cut the cruciform pattern slits into the membranes. Likewise, thermal means could insert the cruciform slits into the membranes.

The volume defined by the inside perimeter surface 16, the top membrane 22, and the bottom membrane 24 contains a lubricant 30. The lubricant could be a water based lubricant, such as the K-Y® Brand Jelly.

The user of the lubrication device 10 inserts the object to be lubricated, such as a penis or a medical apparatus, through the top cruciform slit 26 of the top membrane 22, on through the lubricant 30, and on through the bottom cruciform slit 28 of the bottom membrane 24. By so doing, the lubricant 30 is transferred from the lubrication device 10 onto the inserted object. The user then removes the object from the lubrication device 10. The object is left lubricated.

Figure 11:
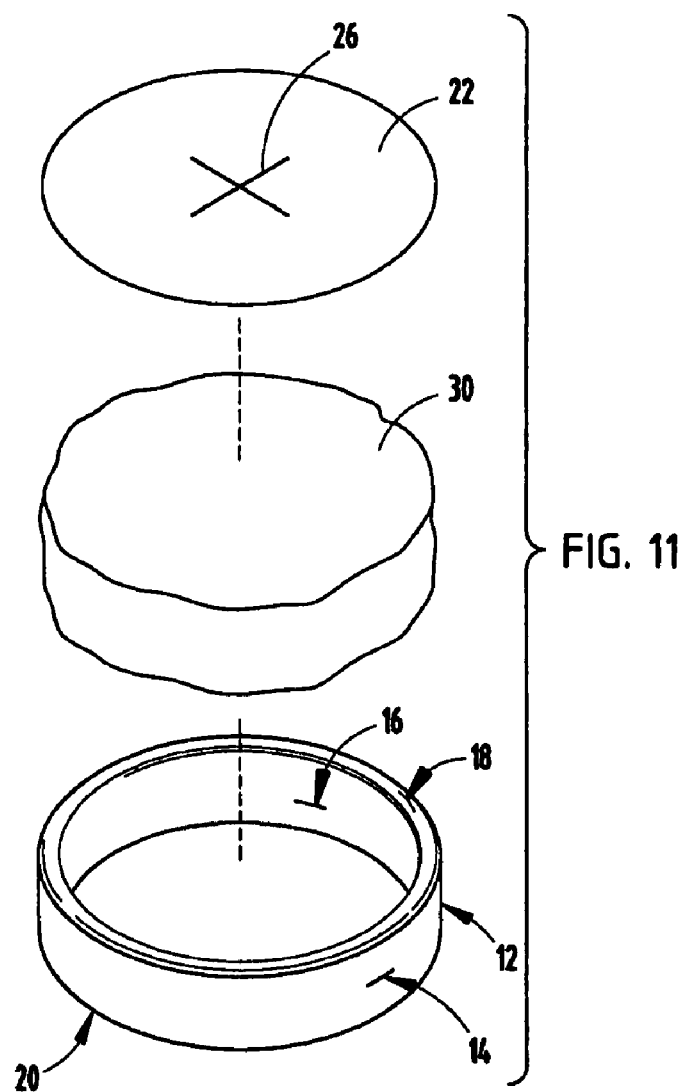
FIG. 11 is an exploded view of a third embodiment of the lubrication device, this time utilizing only one covering material.

A variation of the first embodiment is depicted at FIG. 11. In that variation, the lubrication device 10 does not use a bottom membrane. Rather, there is only a top membrane 22. In that variation, the lubricant 30 is sufficiently viscous or solid so as to not require a bottom membrane to prevent the lubricant 30 from substantially escaping the volume defined by the top membrane 22 and the insider perimeter surface 16. The user of the lubrication device 10 inserts the object to be lubricated, such as a penis or a medical apparatus, through the top cruciform slit 26 of the top membrane 22 and on through the lubricant 30 (or vice-versa). By so doing, the lubricant 30 is transferred from the lubrication device 10 onto the inserted object. The user then removes the object from the lubrication device 10. The object is left lubricated. As explained above, the top penetration zone of the top membrane 22 need not be a cruciform slit but could be defined by any number of intersecting slits.

A second embodiment of the present invention is displayed in FIGS. 6 through 10. The structural support for the lubrication device 10 again is substantially provided by a ring 12. The ring 12, as in the first embodiment, has an outside perimeter surface 14, an inside perimeter surface 16, a top surface 18, and a bottom surface 20. The inside perimeter surface 16 of the ring 12 surrounds a sponge 32. The outside surface 36 of the sponge 32 is permanently attached to the inside perimeter surface 16 of the ring 12. The sponge 32 can be polyurethane foam.

The sponge 32 is saturated with a lubricant. The lubricant can be a water based lubricant, such as the K-Y® Brand Jelly. The sponge 32 can become saturated with a lubricant by compressing the sponge, placing the sponge into lubricant, and decompressing the sponge while lubricant surrounds the sponge. The act of decompressing allows the sponge to draw lubricant into the sponge's interior. Alternatively, the sponge can become lubricated by forcing lubricant into the sponge under pressure.

Figure 13:
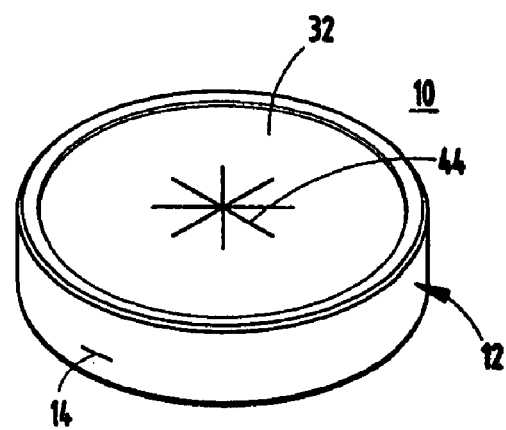
FIG. 13 is a top perspective view of a second embodiment of the lubrication device, where the penetration zone is defined by four intersecting slits rather than a cruciform slit.

The sponge 32 has a penetration zone defined by a cruciform slit 34. The cruciform slit 34 extends entirely through the thickness 38 of the sponge 32. Instead of a cruciform slit 34, the penetration zone of the sponge 32 could be defined by any number of intersecting slits through the thickness 38 of the sponge 32, such as the four intersecting slits 44 depicted at FIG. 13. The sponge 32 can have a thickness 36 of between 0.25 to 0.32 inches, but a thickness 38 as small as 0.125 inches may be feasible. The user lubricates the object to be lubricated by inserting the object through the cruciform slit 34 of the sponge 32. By doing so, the lubricant from the sponge 32 is deposited onto the object. The user then retracts the object from the sponge. The object is left lubricated.

Any of the embodiments of the lubrication device could be sold as a kit, wherein the lubrication device is sealed inside a wrapper, similar to a condom wrapper. The user of the kit could then open the wrapper, remove the lubrication device, and then use the lubrication device for a suitable application such as penis lubrication or to lubricate a medical device. Such medical devices include laparoscopy instruments, which include cameras and lights, and endoscopy instruments, which include endoscopes, before insertion into a human body.

The solutions offered by the invention herein have thus been attained in an economical, practical, and facile manner. While preferred embodiments and example configurations have been shown and described, it is to be understood that various further modifications and additional configurations will be apparent to those skilled in the art. It is intended that the specific embodiments and configurations disclosed are illustrative of the preferred and best modes for practicing the invention, and should not be interpreted as limitations on the scope of the invention as defined by the appended claims and it is to be appreciated that various changes, rearrangements and modifications may be made therein, without departing from the scope of the invention as defined by the appended claims.

The invention claimed is:

1. A lubrication device comprising a ring and a sponge,
   wherein the ring comprises an inside perimeter,
   wherein the sponge comprises a penetration zone and an outside perimeter,
   wherein the outside perimeter of the sponge is adhered to the inside perimeter of the ring, and,
   wherein the sponge is saturated with a lubricant.

2. The lubrication device of claim 1, wherein the penetration zone of the sponge comprises any number of intersecting slits through the thickness of the sponge.

3. The lubrication device of claim 1, wherein the lubricant is water based lubricant.

4. A method of lubricating an object comprising the steps of:
   (a) selecting an object to be lubricated;
   (b) selecting a lubrication device,
      wherein the lubrication device comprises a ring and a sponge,
      wherein the ring comprises an inside perimeter,
      wherein the sponge comprises a penetration zone and an outside perimeter,
      wherein the outside perimeter of the sponge is adhered to the inside perimeter of the ring, and,
      wherein the sponge is saturated with a lubricant;
   (c) inserting the object to be lubricated into the penetration zone of the sponge of the lubrication device; and
   (d) removing the object to be lubricated from the lubrication device.

5. The method of claim 4, wherein the object to be lubricated is a penis.

6. The method of claim 4, wherein the object to be lubricated is a medical device.

7. The method of claim 6, wherein the medical device is a laparoscopy instrument.

8. The method of claim 6, wherein the medical device is an endoscopy instrument.

9. The method of claim 8, wherein the endoscopy instrument is an endoscope.

10. The method of claim 4, further comprising a step (e), which comprises inserting the object to be lubricated, which is now lubricated, into a human body or orifice.

* * * * *